United States Patent [19]

Graether

[11] Patent Number: 4,610,689
[45] Date of Patent: Sep. 9, 1986

[54] INTRAOCULAR LENS

[76] Inventor: John M. Graether, 611 Elmwood, Marshalltown, Iowa 50158

[21] Appl. No.: 518,370

[22] Filed: Jul. 29, 1983

[51] Int. Cl.⁴ .............................................. A61F 2/16
[52] U.S. Cl. ...................................................... 623/6
[58] Field of Search .............................. 3/13; D24/33

[56] References Cited

U.S. PATENT DOCUMENTS

| 4,426,741 | 1/1984 | Bittner | 3/13 |
| 4,435,855 | 3/1984 | Pannu | 3/13 |

FOREIGN PATENT DOCUMENTS

WO83/01538  5/1983  PCT Int'l Appl. ...................... 623/6

Primary Examiner—Richard J. Apley
Assistant Examiner—James Prizant
Attorney, Agent, or Firm—Zarley, McKee, Thomte, Voorhees & Sease

[57] ABSTRACT

An improved surgically replaceable intraocular lens having a generally round lens to which are attached a pair of symmetrical voluted loop members secured to opposite sides of the periphery of lens. Each loop member is comprised of a continuous strand of material having opposite terminal ends secured to the lens and curved outwardly from and substantially parallel to the periphery of the lens; its very distal end curling inwardly to provide a reversed curve or scrolled portion. The greatest width of each loop member is between the points of securement of the terminal ends to the lens, and the loop members are displaced and offset with respect to the posterior plane of the lens.

1 Claim, 6 Drawing Figures

INTRAOCULAR LENS

BACKGROUND OF THE INVENTION

1. Field of the Invention

This invention relates to intraocular lenses and in particular to intraocular lenses having the capability for insertion into the anterior or posterior chamber of the eye and having the capabilities of universal fit.

2. Problems In the Art

Present methods of surgically treating cataracts involve removal and replacement of part or all of the natural eye lens with an artificial intraocular lens. The artificial lens is designed to come as close as possible at mimicking the natural lens and therefore must be securely and stably placed within the eye.

To facilitate the insertion and securement of the artificial lens, support structure must be associated with the artificial lens. Some devices which are still used in certain cases, require suturing the support structure to suitable portions of the eye to hold the lens in place. Aside from the obvious complexity of such implantation, this method makes removal or adjustment of the lens extremely difficult and subjects the eye to additional damage.

Developments led to a less traumatic intraocular lens which utilizes arms or extensions from the lens which fit within the natural boundaries or walls of the eye and hold the lens in place by contact and compressive forces. While some of these devices still utilize sutures to finally secure them in place, many are now being used which, by virtue of their resilient compression and contact with parts of the eye, are non-sutured and self-securing.

Typical examples of such a device are disclosed in Callahan, U.S. Pat. No. 4,363,143 and Kelman, U.S. Pat. No. 4,370,760. All utilize flexible arms extending from the lens body to resiliently hold the lens in place.

Devices such as Sheets, U.S. Pat. No. 4,328,595, utilize flexible support loops having proximal ends fused or inserted into the lens body.

Although there are many different types of intraocular lenses in use and available for use, problems within the art still exist.

Many existing lenses are usable for certain size eyes and therefore must be manufactured in many different sizes. This requires surgeons to keep a large inventory of lenses. Secondly, many of the devices are specifically designed for either anterior placement or posterior placement. Again, this requires the surgeon to have the requisite inventory to satisfy the needs of various patients. Existing, so called "universal lenses" (Duolens, Shepard Universal, Pannu) are either excessively fragile, difficult to insert in one or both locations, or lack vaulting to separate the lens from the iris or capsule. Several are totally dependent on a single filament for support and if fractured would result in the collapse of the lens requiring immediate removal.

Another major problem with existing intraocular lenses involves contact and irritation of the eye by the support structure of these devices, or even the lens itself. This might result from the position of the lens once implanted or may result from contact of the support structure. One method by which some prior art devices attempt to minimize such problems is by having support structure which biases or resiliently urges the lens body posteriorly in an attempt to force the lens body back towards the posterior capsule and away from the iris.

A disadvantage produced by holding the lens towards the posterior capsule exists in the fact that once implanted, additional surgery is many times needed. Modern methods of surgery increasingly utilize lasers to facilitate this surgery. If the lens body is biased towards the posterior capsule, as is the case with many of the existing devices, laser surgery of the posterior capsule is more difficult, if not precluded, and the lens is exposed to a great risk of damage. An elevation slightly from the posterior capsule facilitates YAG laser capsulotomy while still avoiding the risk of pupil capture. It also allows sufficient clearance for YAG laser photocoagulation.

With many self-supporting intraocular lenses, the support structure does not sufficiently have the ability to compress to different sizes of eyes, while at the same time both minimizing compression forces and preventing tilt or torque and presenting relatively easy insertion capabilities and sufficient fixation of the lens body so that pupil capture is prevented.

Another disadvantage of many of the present devices is that the stability of the lens is sacrificed in order to obtain more flexible, universal fit lenses. Likewise, many of the present devices cannot be easily insertable and maneuverable with one instrument and many are totally dependent for support on one fragile strut or filament.

SUMMARY OF THE INVENTION

The present invention utilizes a conventional intraocular lens suitable for use as an artificial lens implant. A pair of symmetrical loop members are secured to the periphery of the lens to secure and self-support the lens in the eye. Each loop member is comprised of a continuous strand of material having opposite terminal ends secured to the lens. The terminal ends are spaced apart on the periphery of the lens, the lateral width of the loop being greatest at the points where the ends are secured to the lens. The closed loop members are positioned opposite each other with respect to the center of the lens, their distal ends extending outwardly and curving back in towards the lens, both in the same direction of curve so that from distal-end-to-distal-end of the loop members, an S-shape is formed, with the lens in the center. The loop members generally curve substantially outwardly from and laterally to, each loop in an opposite direction to the periphery of the lens; the very distal end of the loop members being curved more radically inward and in a direction towards the lens to provide a reversed curved portion. The proximal terminal ends of the loop members can be attached to the lens in a manner so that initially they are directed at an angle posterior to the lens. The distal portion of the loop members are then bent back into a plane behind but parallel to the posterior plane of the lens.

The voluted or scroll reverse curve portion at each distal end of the loops thus provides new and improved advantages over the prior art. It is flexible enough to allow for a universal fit in various shaped and sized eyes and yet retains low and relatively linear compression characteristics. The compression characteristics allow for gradual alteration of loop shape without significant displacement of the loop or lens body from their respective planes, thus inhibiting tilting or torquing of the lens. Also, the loop shape provides a large area of capsule contact for compression and support with minimal stress on the capsule itself. The special shape of the curve provides consistent centering of the lens, provides improved ability for control during insertion using a single instrument, and allows anterior chamber or posterior chamber insertion. The invention can even function effectively with one loop in the capsule and one loop in the sulcus.

The broad-based loop fixation points on the lens provide superior and improved stability for correct optical alignment, uniform separation of the lens from the capsule to facilitate surgical or YAG capsulotomy, and also presents limited exposure of the free edge of the lens and helps prevent tilting to prevent pupil capture or induce optical abberation.

The two-plane configuration of the loop and the posterior of the lens allows separation of the lens optic from the capsule in the posterior chamber without the necessity of ridges or tabs on the lens, allows for the surgical or YAG laser capsulotomy, and avoids contact of the loop or optic with the mobile iris sphincter when the lens is used in the anterior chamber.

The lens configuration and materials make it equally suitable for implantation in the anterior chamber as well as in the posterior chamber, either in the ciliary sulcus or within the remnants of the lens capsule. The loop material is not subject to biodegradation or actinic degradation when exposed to light in the anterior chamber for extended periods as are loops of nylon or polypropylene. This versitility greatly reduces the surgeon's inventory requirements.

It is therefore a principal object of the invention to provide a new and improved intraocular lens.

It is another object of the present invention to provide an intraocular lens which improves over the deficiencies in the art.

A further object of the invention is to provide an intraocular lens which has support structure which allows universal fit of the lens, whether inserted in the anterior chamber or posterior chamber of the eye.

Another object of the invention is to provide in intraocular lens which provides greater stability after insertion.

A further object of the invention is to provide an intraocular lens which provides improved ability for correct optical alignment.

A further object of this invention is to provide an intraocular lens which provides improved uniform separation of the lens from the capsule.

Another object of the invention is to provide an intraocular lens which limits exposure of the free edge of the lens and avoids tilting or torquing to prevent pupil capture.

Another object of the invention is to provide an intraocular lens which provides improved capability for control during insertion and improved capability for insertion with one instrument.

Another object of the invention is to provide an intraocular lens which has low and relatively linear compression characteristics, allows gradual alteration of loop shape during compression without significant displacement of loop or lens body from their respective planes, at the same time preventing excessive compression or collapse of the loops beyond the point that is useful for lens insertion or support. The design also allows a large area of capsule contact for compression and support with minimal stress on the capsule.

Another object of the invention is to provide an intraocular lens which maintains the lens in an offset plane anteriorly of the supporting loops to allow for laser surgery of the posterior capsule and to avoid contact of the loop or optic with the mobile iris sphincter when the lens is used in the anterior chamber.

A further object of this invention is to provide an intraocular lens which is equally suitable for implantation in the anterior chamber as well as in the posterior chamber, either in the ciliary sulcus or within the remnants of the lens capsule.

Another object of this invention is to provide an intraocular lens which is improved consistency and accuracy in centering the lens within the eye.

These and other objects and advantages of the invention will become apparent with reference to the accompanying drawings and descriptions.

DETAILED DESCRIPTION OF THE PREFERRED EMBODIMENT

The preferred embodiment of the invention can be seen with reference to the accompanying drawing figures.

Figure 1:
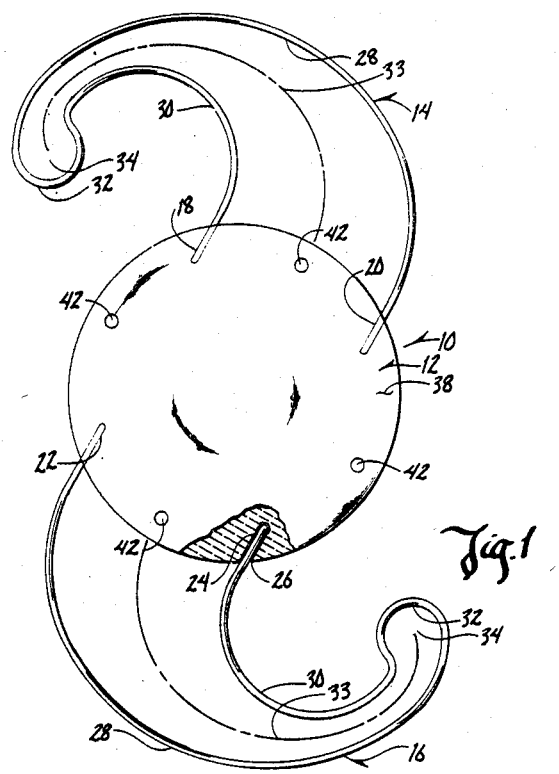
FIG. 1 is a plan view of the invention with a portion cutaway showing the attachment of one of the terminal ends of one of the loops.

In FIG. 1, an intraocular lens 10 is shown in accordance with the invention and includes a medial light focusing lens body or optic 12 having a generally circular perimeter. Flexible and resilient loop members 14 and 16 extend symmetrically in a voluted shape from opposite sides of the perimeter of lens body 12 and provide support and retention of lens body 12 when the invention 10 is inserted and implanted into a patient's eye. Loop members 14 and 16 are continuous strands of thread-like material, in the preferred embodiment being made of 0.15 millimeter diameter methyl methacrylate or PMMA, which is durable and resilient, yet is flexible. Methyl Methacrylate is also very resistant to degradation by ultraviolet light when used in the anterior chamber.

The terminal ends 18, 20 of loop member 14 and 22, 24 of loop member 16 are secured to lens body 12 by insertion into pre-drilled channels 26 as can be seen in the cutaway portion of FIG. 1. The terminal ends are bonded in channels 26 by a heat probe or ultrasonic probe or any conventional manner of fusing.

Loop members 14 and 16 extend from terminal ends 18, 20 and 22, 24, respectively, to curved portions consisting of an outer curved portion 28 and an inner curved portion 30 which extend and curve generally along a longitudinal axis 33 in a direction somewhat concentric to the perimeter of lens body 12. Outer curved portion 28 and inner curved portion 30 of both loop members 14 and 16 continually narrow as to one another and are joined at a distal end portion 32. Distal end portion 32 defines a generally circular space 34 which is somewhat wider than the space between the immediately adjacent inner curved portion 30 and outer curved portion 28. Distal end portion 32 actually curves more radically back towards the respective loop member 14 or 16, forming what will be called a reverse curve. The reverse curve allows the long outer edge of outer curved portion 28 to be the contacting portions of loop members 14, 16 with the eye when implanted, thereby providing increased contact and stability. Circular space 34 allows access for the Graether Collar Button Iris Retractor shown in FIGS. 5 and 6. This instrument provides simultaneous compression and rotation of the lens for placement of the loops in the anterior chamber, the ciliary sulcus, or within the capsule remnants.

Explained differently, loop members 14 and 16 are centered along a longitudinal axis 33 which curvingly extends outwardly from lens body 12. The middle and outer parts of each longitudinal axis 33 curve generally in a direction somewhat concentric to the perimeter of lens body 12, except for the extreme outward end of longitudinal axis 33, which curves more radically towards lens body 12. The longitudinal axis 33 passes directly through the center of circular space 34.

Distal end portions 32 are generally positioned on opposite sides of lens body 12 along a diameter line extending through the center of lens body 12. In the preferred embodiment, distal end portions 32 of loop members 14 and 16 will exist generally along an extended diameter line of lens body 12, over a range from a fully relaxed extended state to a position where distal ends portions 32 are immediatly adjacent lens body 12. Thus, distal end portions 32 will generally exist along an extended diameter line of lens body 12 regardless of the state of compression of loop members 14 and 16.

In the preferred embodiment, the lens body 12 is approximately 6 millimeters in diameter and the maximum length from end-to-end of the invention 10 in a fully extended pre-insertion state is 13.5 to 14 millimeters. It is also preferred that lens body 12 be made of optical plastic such as methyl methacrylate so that all parts of invention 10 are made of the same material. Lens body 12 is preferred to be aspheric with ultraviolet absorbing capacities.

Figure 5:
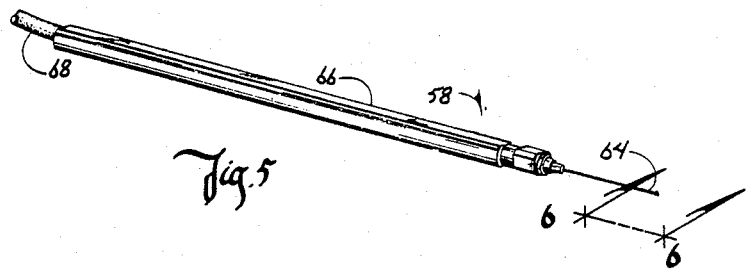
FIG. 5 is a perspective view of an ophthalmologic instrument which can be used for insertion and manipulation of the invention.
Figure 6:
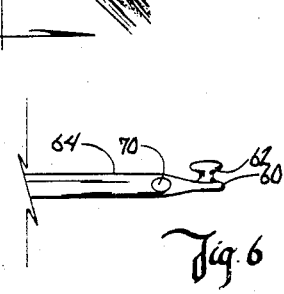
FIG. 6 is a side elevation view taken along line 6—6 of FIG. 5.

The voluted or scroll shape of reverse curve loop members 14 and 16 provide a locus for the control of the lens movement during insertion and facilitate the use of a single instrument, such as the Graether Collar Button Iris Retractor shown in FIGS. 5 and 6. The material of construction and the shape of the curved loops provide low and relatively linear compression characteristics from the appliance's maximum diameter of approximately 14 millimeters down to a 10 millimeter diameter. This is extremely advantageous in avoiding any damage to the contacted portions of the eye. The large area of capsule or sulcus contact by the outer curved portions 28 of loop members 14, 16 provide for improved compression and support with minimal stress on the capsule or sulcus, additionally allowing consistent centering of the lens, whether placed in the capsule remnants or in the ciliary sulcus.

The reverse curved shape of loop members 14, 16 also allows for gradual alteration of loop shape during compression without significant displacement of the loop or lens body from their respective planes. This compression is accomplished in part by a gradual curling up of the scrolled portion of the loop until portion 28 contacts portion 30. At that point compression forces increase providing resistance to an undesirable collapse of the loop beyond a diameter necessary for insertion. This characteristic provides protection against kinking of the material, thus exceeding its elastic limit and reducing its resiliency. The smoothly curved methyl methacrylate loops facilitate rotation of the lens 10, either clockwise or counterclockwise, within the capsule or sulcus without frictional damage.

In the preferred embodiment, outer curved portions 28 are positioned radially 4.2 millimeters from the interior end of pre-drilled insertion hole 26 of inner curved portions 30. Inner curved portions 30 are positioned along an arc having a radius of 1.3 millimeters centered on a point approximately midway between distal portion 32 and terminal end 18 or 24. Distal portions 32 are defined by a 0.6 millimeter radius taken from the center of circular opening 34. At its widest lateral width, each loop member 14, 16 is 7.6 millimeters wide, in its uncompressed state.

Figure 2:
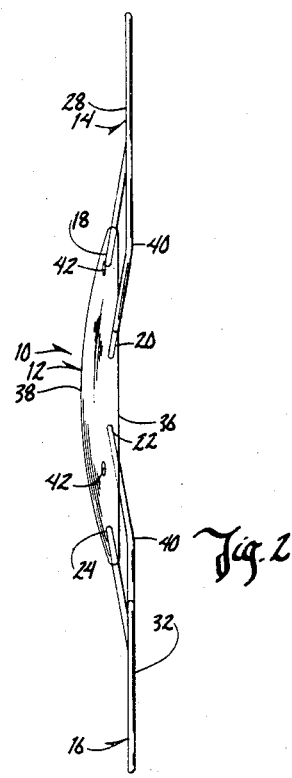
FIG. 2 is a side elevational view of the invention.

By referring to FIG. 2, it can be seen that loop members 14, 16 are offset from the posterior surface 36 of lens body 12. Posterior surface 36 is generally planar whereas anterior surface 38 is molded or machined to a desired spherical or convex shape according to the required optical characteristics for a particular patient in which it is to be implanted.

Outer curved portions 28, inner curved portions 30 and distal end portions 32 of loop members 14, 16 are positioned in the offset plane to that of posterior surface 36 by angling terminal ends 18, 20, 22 and 24 outwardly and posteriorly of lens body 12. This is facilitated by drilling pre-drilled channels 26 into lens body 12 at approximately 10° from the plane defined by posterior surface 36. The angle at which pre-drilled channels 26 are drilled can be modified to choice, but in the preferred embodiment, channels 26 are generally angled up parallel with the anterior surface 38 of lens body 12. Terminal ends 18, 20, 22 and 24 then extend outwardly and posteriorly to bend points 40 (bend points 40 for outer curved portion 28 of loop member 16 and inner curved portion 30 of loop number 14 cannot be seen in FIG. 2) which are pre-manufactured into the loop members 14 and 16. The portions of loop members 14 and 16 which are parallel to posterior surface 36 are preferred to be offset from posterior surface 36 a minimum of 0.3 millimeters to a maximum of 0.5 millimeters. This causes the posterior surface 36 of lens body 12 to be elevated off the capsule upon implantation and provides separation of the lens optic from the capsule in the posterior chamber without the necessity of ridges or tabs on the lens optic. If the invention 10 is inserted in the anterior chamber, the vaulting or offset into the two plane configuration avoids contact of the loop or optic with the mobile iris sphincter.

It is to be noted that the closed reversed curved loop of loop members 14 and 16 is widest across the lateral distance between terminal ends 18, 20 and 20, 24. These broad-based loop insertion or fixation points achieve stability of the lens optic 12 and provide correct optical alignment. The stability also achieves uniform separation of the lens from the capsule to facilitate surgical or YAG laser capsulotomy. Tilting or torquing is avoided and limited exposure of the free edge of the lens prevents pupil capture.

Positioning holes 42 can optionally be placed around the perimetric edge of lens body 12 as peripherally as practical; preferably no greater than 0.5 millimeter interiorly of the edge of lens body 12. Positioning holes 34 are preferred to be approximately 3.5 millimeters in diameter and are used with an instrument such as a Sinskey hook or bent needle for positioning or rotation. It is to be understood that positioning holes 42 may be redundant, and unnecessary, in that the invention 10 is easily manipulated by utilizing an instrument such as shown in FIGS. 5 and 6, placed in circular space 34.

Figure 3:
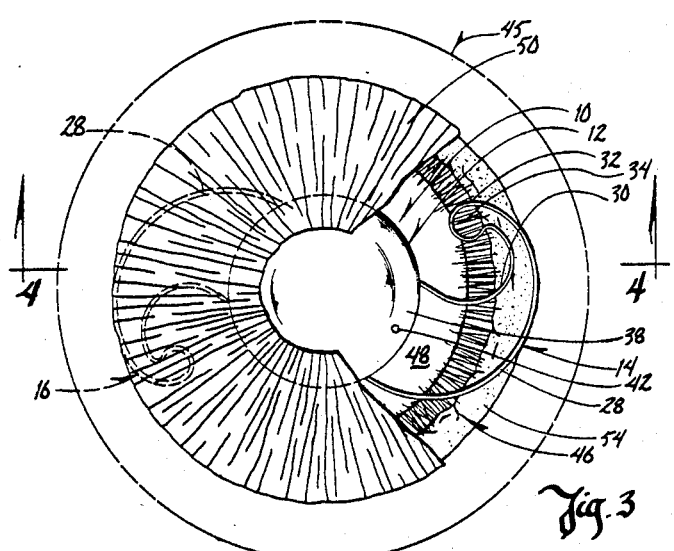
FIG. 3 is a front plan view of the invention after insertion within the eye, with a partial cutaway showing the interior of the eye, and is taken from line 3—3 of FIG. 4.
Figure 4:
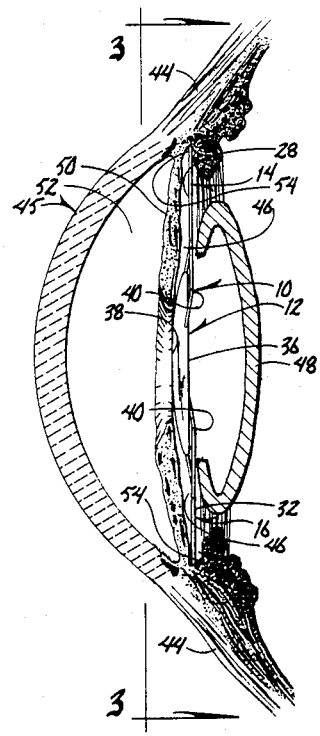
FIG. 4 is a sectional view taken from line 4—4 of FIG. 3.

By referring to FIGS. 3 and 4, the invention 10, as implanted into an eye 45, can be described.

Preparation of the eye 45 for receipt of the invention 10 begins with conventional extracapsular cataract extraction procedure which includes an incision through the sclera 44 of sufficient width to gain access to the interior of the eye and to insert the invention 10.

Implantment into the posterior chamber 46 means that loop members 14 and 16 contact the edges of the posterior chamber 46, namely the cilius sulcus 54, and resiliently, because of compression of loop members 14 and 16 hold the invention 10 in place along the optical axis of the eye in a position closely corresponding with the position of the original natural lens. As can be seen in FIG. 4, the anterior portion of lens capsule 48 has been removed by the surgery and the intraocular lens 10 is placed immediately in front of capsule 48 in the posterior chamber 46, immediately behind iris 50.

FIG. 3 illustrates how the reverse curved loop members 14 and 16 center lens body 12 and can facilitate a universal fit for various sizes of eyes. The large contact length of outer curved portions 28 of loop members 14 and 16 provide a stable and secure fit while the broad-based loop insertion or fixation points of terminal ends 18, 20, 22 and 24 provide stability and prevent tilting. The configuration of intraocular lens 10 and the materials from which it is made make it equally suitable for implantation in the anterior chamber 52 as well as in the posterior chamber 46. Furthermore, posterior chamber implantment allows for placement of loops 14, 16 either in the ciliary sulcus 54 or within the remnants of the lens capsule 48. Such versatility provides flexibility for the surgeon and greatly reduces inventory requirements. The compressible nature of loop members 14 and 16 allow for insertion in virtually any conventional sized eye.

The small and flexible nature of loop members 14 and 16 allow the invention 10 to be easily inserted through a small incision into the eye, and easily maneuvered once in. No sutures or similar extraneous securing hardware is needed which simplifies the procedure and makes removal easier if required.

It is to be noted that a large number of persons require second surgery after extracapsular cataract extraction. Therefore, a prime advantage of the invention 10 is its vaulted characteristic which allows for post-insertion surgical or YAG laser capsulotomy, greatly reducing the chances of damage to the lens body 12 or loop members 14 and 16.

Manipulation of the invention 10 can be easily and efficiently accomplished by use of instrument 58 shown in FIGS. 5 and 6. By referring specifically to FIG. 6, it can be seen that instrument 58 has a handle 66 from one end of which extends stem 64 having a bluntly pointed end 60 and a perpendicular flared portion 62. Handle 66 and stem 64 have channels extending therethrough and an irrigation line 68 enters the end of handle 66 opposite from stem 64 and is in fluid communication with irrigation aperture 70 in stem 64. One instrument manipulation can be executed, one method being to insert the perpendicular portion 62 of instrument 58 into circular opening 34 of distal portion 32 of one of loops 14 or 16. The lens diameter can then be reduced within the eye by bringing the portion 32 toward positioning hole 42 thus compressing the proximal loop while the distal loop is compressed by the tissue. The compressed lens can be rotated in either direction by appropriate pressure of the instrument against loop distal end portion 32 delivering the lens into the appropriate position within the capsule or chamber. It is usual to rotate the lens 10, 90° into the lateral pockets of the capsule or the lateral sulcus as shown in FIG. 3, to insure consistent and accurate centering. Instrument 58, also known as the Graether Collar Button Iris Retractor, is the preferred tool for use in insertion of invention 10. However, other instruments such as the Kugen Retractor or the Lester Spindle Manipulator could also be used.

It is to be understood that this is the preferred embodiment of the invention only and does not limit or confine the invention. Changes and modifications can be made in the invention staying within the scope of the invention as defined by the following claims.

What is claimed is:

1. In a surgically replacement intraocular lens, comprising:

a lens body having an outer periphery;

a pair of compresible, resilient symmetrical loop members secured to the periphery of said lens body and being symmetrically positioned opposite each other with respect to the center of the lens body;

each loop member being comprised of a continuous strand of material having opposite parallel widely spaced terminal ends secured to said lens body, and extending outwardly in a closed loop to a distal end portion and dwelling in a position spaced from and substantially parallel to the periphery of the lens body;

the lateral width of said loop member being the greatest at the points where said terminal ends are secured to said lens body, and continually narrowing between said lens body and said distal end portion;

each terminal end of one of said loop members being in planar alignment with one each of the terminal ends of the other of said loop members, said distal end portion being curved inwardly in a direction towards said lens body to provide a reversed curve portion;

said continuous strand of material comprising an inner curved portion spaced from an outer curved portion with said distal end portion therebetween;

said distal end portion defining a generally circular space communicating with the space between said inner and outer curved portions and having a diameter greater than the distance between said inner curved portion and said outer curved portion immediately adjacent said distal end portion.

* * * * *